(12) United States Patent
Chang et al.

(10) Patent No.: US 7,741,498 B2
(45) Date of Patent: Jun. 22, 2010

(54) PROPYLENE OXIDE PROCESS

(75) Inventors: Te Chang, West Chester, PA (US); Gary A. Sawyer, Media, PA (US)

(73) Assignee: Lyondell Chemical Technology, L.P., Greenville, DE (US)

( * ) Notice: Subject to any disclaimer, the term of this patent is extended or adjusted under 35 U.S.C. 154(b) by 0 days.

(21) Appl. No.: 12/231,220

(22) Filed: Aug. 29, 2008

(65) Prior Publication Data

US 2010/0056814 A1 Mar. 4, 2010

(51) Int. Cl.
*C07D 301/06* (2006.01)
(52) U.S. Cl. ...................... 549/532; 549/533
(58) Field of Classification Search ............... 549/532, 549/533, 534; 502/66, 325, 347
See application file for complete search history.

(56) References Cited

U.S. PATENT DOCUMENTS

| | | | |
|---|---|---|---|
| 4,954,325 A | 9/1990 | Rubin et al. | |
| 5,849,938 A | 12/1998 | Rueter et al. | |
| 5,973,171 A | 10/1999 | Cochran et al. | |
| 6,077,498 A | 6/2000 | Diaz Cabañas et al. | |
| 6,114,551 A | 9/2000 | Levin et al. | |
| 7,138,535 B1 | 11/2006 | Whitman et al. | |
| 2007/0260075 A1 * | 11/2007 | Jubin et al. | 549/533 |

FOREIGN PATENT DOCUMENTS

| BE | 1001038 A7 | 6/1989 |
|---|---|---|
| WO | WO 2007/050678 | 5/2007 |
| WO | WO 2007/073488 | 7/2007 |

OTHER PUBLICATIONS

R. Szostak, "Non-aluminosilicate molecular sieves," in Molecular sieves: Principles of synthesis and identification (1989), p. 205, Van Nostrand Reinhold.
G. Vayssilov, "Structural and physicochemical features of titanium silicalites", in Catal. Rev.-Sci. Eng., (1997). p. 209, vol. 39(3).
T. Maschmeyer et al., "Heterogeneous catalysts obtained by grafting metallocene complexes onto mesoporous silica", in Nature, (Nov. 1995), p. 159, vol. 378 (9).
P. T. Tanev et al., "Titanium-containing mesoporous molecular sieves for catalytic oxidation of aromatic compounds", in Nature, (Mar. 1994), p. 321, vol. 368.
A. Corma et al., J. Chem.Soc., Chem. Commun., (1998), p. 579.
D. Wei et al., "Catalytic behavior of vanadium substituted mesoporous molecular sieves", in Catal. Today, (1999), pp. 501, vol. 51.
W. Laufer et al., "Direct oxidation of propylene and other olenfins on precious metal containing Tl-catalysts," *Applied Catalysis A: General*, Elsevier Science, vol. 213, (2001), pp. 163-171.

\* cited by examiner

*Primary Examiner*—Janet L. Andres
*Assistant Examiner*—David E Gallis
(74) *Attorney, Agent, or Firm*—Yuanzhang Han

(57) ABSTRACT

A process for making propylene oxide from propylene is disclosed. The process comprises reacting propylene, oxygen, and hydrogen in the presence of a catalyst and a solvent to produce a reaction mixture comprising propylene oxide. Separation of propylene, oxygen, hydrogen, and propylene oxide from the reaction mixture results in a residual mixture comprising methanol. A portion of the residual mixture is recycled to the reaction. A portion of the residual mixture is distilled to generate a distilled methanol stream, which is recycled to the reaction.

9 Claims, 1 Drawing Sheet

PROPYLENE OXIDE PROCESS

FIELD OF THE INVENTION

The invention relates to a process for producing propylene oxide by reacting propylene, oxygen, and hydrogen in the presence of a catalyst and a solvent.

BACKGROUND OF THE INVENTION

Propylene oxide is an important industrial chemical intermediate. Propylene oxide can be produced by direct epoxidation of propylene with oxygen and hydrogen in a solvent in the presence of a catalyst (U.S. Pat. Nos. 7,138,535 and 5,973,171). U.S. Pat. No. 5,973,171 additionally teaches recovering methanol solvent from the reaction mixture and recycling the recovered solvent to the epoxidation reaction.

SUMMARY OF THE INVENTION

The invention is a process for making propylene oxide from propylene, oxygen, and hydrogen. The process comprises reacting propylene, oxygen, and hydrogen in the presence of a catalyst and a solvent to produce a reaction mixture comprising propylene oxide. Separation of propylene, oxygen, hydrogen, and propylene oxide from the reaction mixture results in a residual mixture comprising methanol. A portion of the residual mixture is recycled to the epoxidation reaction. The rest of the residual mixture is distilled to generate a distilled methanol stream, which is recycled to the epoxidation. The weight of methanol to water in the reaction mixture is greater than 7:3.

DETAILED DESCRIPTION OF THE INVENTION

Figure 1:
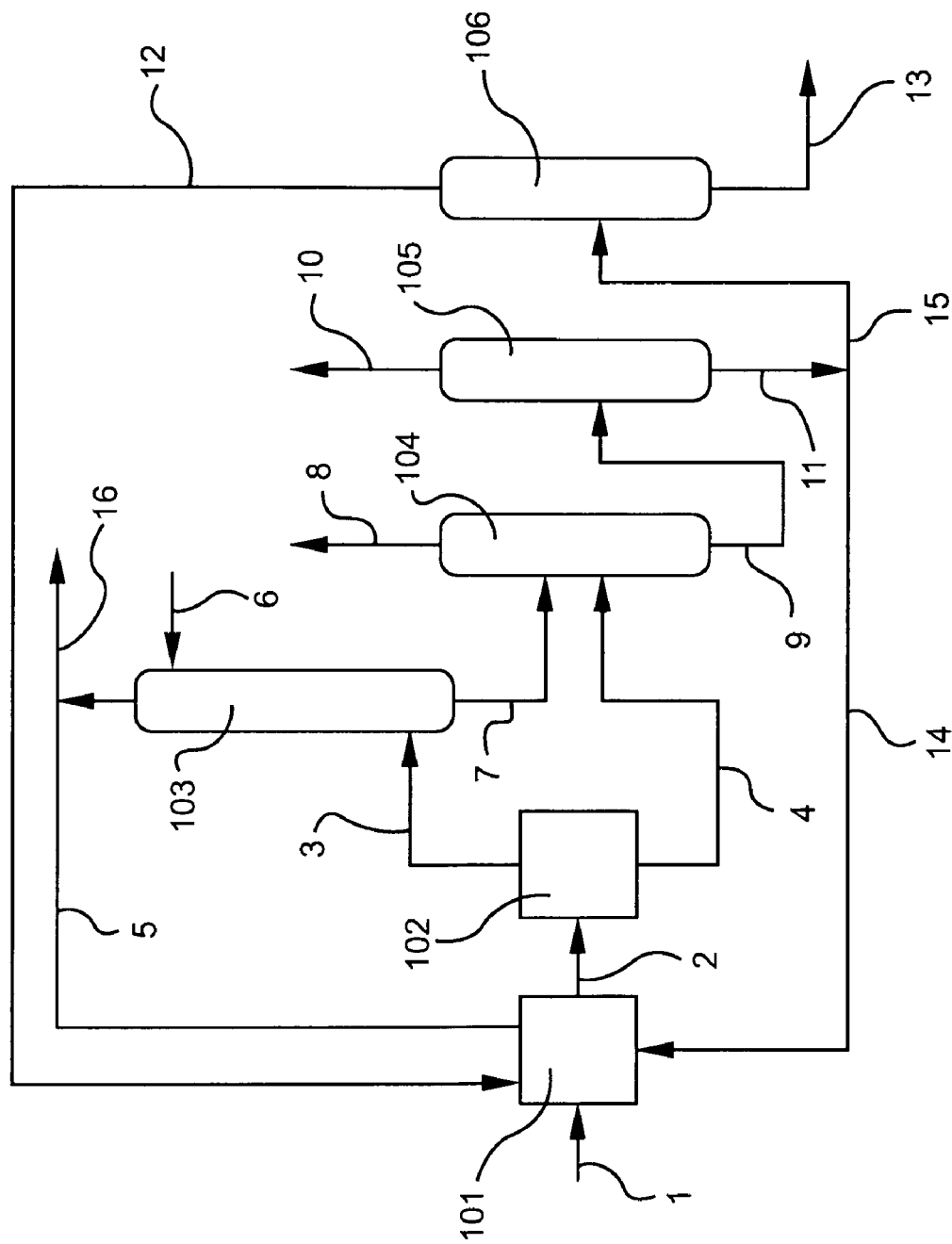
FIG. 1 is a schematic presentation of one embodiment of the present invention.

The process comprises reacting propylene, oxygen, and hydrogen in the presence of a catalyst ("the reaction step"). A suitable catalyst comprises a transition metal zeolite and a noble metal. Zeolites generally contain one or more of Si, Ge, Al, B, P, or the like, in addition to oxygen. A transition metal zeolite (e.g., titanium zeolite, vanadium zeolite) is a crystalline material having a porous molecular sieve structure and containing a transition metal. A transition metal is a Group 3-12 element. The first row of these includes elements from Sc to Zn. Preferred transition metals are Ti, V, Mn, Fe, Co, Cr, Zr, Nb, Mo, and W. Particularly preferred are Ti, V, Mo, and W. Most preferred is Ti. Titanium silicalite-1 (TS-1, a titanium silicalite having an MFI topology analogous to that of the ZSM-5 aluminosilicate) is particularly preferred.

Suitable titanium zeolites include titanium silicates (titanosilicates). Preferably, they contain no element other than titanium, silicon, and oxygen in the lattice framework (see R. Szostak, "Non-aluminosilicate Molecular Sieves," in *Molecular Sieves: Principles of Synthesis and Identification* (1989), Van Nostrand Reinhold, pp. 205-282). Small amounts of impurities, e.g., boron, iron, aluminum, phosphorous, copper, and mixtures thereof, may be present in the lattice. The amount of impurities is preferably less than 0.5 weight percent (wt %), more preferably less than 0.1 wt %. Preferred titanium silicates will generally have a composition corresponding to the following empirical formula: $xTiO_2 \cdot (1-x)SiO_2$, where x is between 0.0001 and 0.5. More preferably, the value of x is from 0.01 to 0.125. The molar ratio of silicon to titanium in the lattice framework of the zeolite is advantageously from 9.5:1 to 99:1 (most preferably from 9.5:1 to 60:1). The use of relatively titanium-rich zeolites may also be desirable. Particularly preferred titanium zeolites include the class of molecular sieves commonly known as titanium silicalites (see *Catal. Rev.-Sci. Eng.* 39(3) (1997) 209). Examples of these include TS-1, TS-2 (having an MEL topology analogous to that of the ZSM-11 aluminosilicate), and TS-3 (as described in Belgian Pat. No. 1,001,038). Titanium zeolites having framework structures isomorphous to zeolite beta, mordenite, ZSM-12, MCM-22, MCM-41, and MCM-48 are also suitable for use. Examples of MCM-22, MCM-41, and MCM-48 zeolites are described in U.S. Pat. Nos. 4,954,325, 6,077,498, and 6,114,551; Maschmeyer, T., et al, *Nature* 378(9) (1995) 159; Tanev, P. T., et al., *Nature* 368 (1994) 321; Corma, A., *J. Chem. Soc., Chem. Commun.* (1998) 579; Wei D., et al., *Catal. Today* 51 (1999) 501). The most preferred is TS-1.

Suitable noble metals include, e.g., gold, silver, platinum, palladium, iridium, ruthenium, rhenium, rhodium, osmium, and mixtures thereof. Preferred noble metals are Pd, Pt, Au, Re, Ag, and mixtures thereof. A catalyst comprising palladium is particularly preferred. Typically, the amount of noble metal present in the catalyst is in the range of from 0.01 to 20 wt %, preferably from 0.1 to 5 wt %.

The noble metal and the transition metal zeolite may be on a single particle or on separate ones. For example, the noble metal may be supported on the transition metal zeolite. Alternatively, the catalyst may comprise a mixture of a transition metal zeolite and a noble metal supported on a carrier. Suitable carriers for the supported noble metal include carbons, titanias, zirconias, niobias, silicas, aluminas, silica-aluminas, titania-silicas, ion-exchange resins, and the like, and mixtures thereof.

The manner in which the noble metal is incorporated into the catalyst is not critical. For example, the noble metal may be supported on the transition metal zeolite or other carriers by impregnation, ion exchange, adsorption, precipitation, or the like.

The weight ratio of the transition metal zeolite to the noble metal is not particularly critical. However, a transition metal zeolite to noble metal weight ratio of from 10:1 to 10,000:1 is preferred.

The catalyst may be a powder or particles of various shapes and sizes. Suitable catalysts have a particle size in the range of about 0.0001 to about 3 mm. The catalyst may be formed into particles by pelletization, spray-drying, extrudation, and the like.

The process uses propylene. Any gas comprising propylene may be used. Typically, it comprises greater than 90 wt % propylene. Preferably, it comprises greater than 95 wt % propylene. A mixture of propylene and propane may be used.

The process uses oxygen. Any gas comprising oxygen may be used. Typically, it comprises greater than 10 wt % oxygen. Preferably, it comprises greater than 90 wt % oxygen.

The process uses hydrogen. Any gas comprising hydrogen may be used. Typically, it comprises greater than 10 wt % hydrogen. Preferably, it comprises greater than 90 wt % hydrogen.

The molar ratio of hydrogen to oxygen can usually be varied in the range of 1:100 to 10:1 and is especially favorable at 1:5 to 2:1. The molar ratio of oxygen to propylene is usually 1:1 to 1:20, and preferably 1:1.5 to 1:10.

In addition to propylene, oxygen, and hydrogen, a diluent gas may be used. Suitable diluent gases include nitrogen, helium, argon, carbon dioxide, and saturated hydrocarbons (e.g., methane, ethane, propane, and n-butane). Mixtures of those diluent gases can be used. The molar ratio of propylene to diluent gas is usually in the range of 100:1 to 1:20, especially 20:1 to 1:20.

The process uses methanol as a solvent. In addition to methanol, water may be used as a co-solvent.

The process may use a buffer. The buffer can inhibit the formation of propylene glycols or glycol ethers during the epoxidation and improve the reaction rate and selectivities. The buffer is typically added to the solvent to form a buffer solution, or the solvent and the buffer are added separately. Useful buffers include any suitable salts of oxyacids, the nature and proportions of which in the mixture are such that the pH of their solutions preferably ranges from 3 to 12, more preferably from 4 to 10, and most preferably from 5 to 9. Suitable salts of oxyacids contain an anion and a cation. The anion may include phosphate, carbonate, bicarbonate, sulfate, carboxylates (e.g., acetate), borate, hydroxide, silicate, aluminosilicate, or the like. The cation may include ammonium, alkylammonium (e.g., tetraalkylammoniums, pyridiniums), alkylphosphonium, alkali metal, and alkaline earth metal ions, or the like. Examples include $NH_4$, $NBu_4$, $NMe_4$, Li, Na, K, Cs, Mg, and Ca cations. The preferred buffer comprises an anion selected from the group consisting of phosphate, carbonate, bicarbonate, sulfate, hydroxide, and acetate; and a cation selected from the group consisting of ammonium, alkylammonium, alkylphosphonium, alkali metal, and alkaline earth metal ions. Buffers may preferably contain a combination of more than one suitable salt. Typically, the concentration of the buffer in the solvent is from 0.0001 M to 1 M, preferably from 0.0005 M to 0.3 M. More preferred buffers include alkali metal phosphates and ammonium phosphates. The ammonium phosphates buffer is particularly preferred. For example, a buffer comprising an ammonium ion and phosphate ion in a molar ratio of 1:1 to 3:1 may be used.

The reaction step is typically performed at a temperature in the range of from 30 to 100° C., preferably in the range of from 50 to 70° C., and at a pressure in the range of from 100 to 800 psig, preferably in the range of from 150 to 400 psig.

The catalyst is preferably in the form of a suspension or a fixed bed. The process may be performed in a continuous-flow, semi-batch, or batch mode. A continuous-flow process is preferred.

The reaction step produces a reaction mixture comprising propylene, propane, propylene oxide, hydrogen, oxygen, methanol, water, buffer if used, and other byproducts. The weight ratio of methanol to water in the reaction mixture is greater than 7:3, preferably greater than 8:2, because higher concentration of water increase the propylene oxide ring-opening reactions to glycols and/or glycol ethers. See Examples 3 and 4.

The process comprises separating propylene, propane, propylene oxide, hydrogen, oxygen, and diluent gas if used from the reaction mixture to generate a residual mixture comprising methanol, water, and buffer if used. Many different methods may be used for the separation. In one method, light components including propylene, propane, propylene oxide, hydrogen, oxygen, and diluent gas are distilled from the mixture in an initial step to leave a residual mixture behind. Propylene oxide may be separated and purified. Propylene, propane, hydrogen, oxygen, and diluent gas may be recycled to the reaction step. In another method, the separation includes a flash separation, a propylene oxide absorption, a depropanization (separating propylene and propane by distillation), and a crude propylene oxide recovery steps. Such a method is illustrated in FIG. 1, where a mixture of water and methanol is used as the solvent for the epoxidation of propylene. A feed (via lines 1, 12, and 14) comprising propylene, oxygen, hydrogen, methanol, water, and a buffer solution is fed to reactor 101 and reacted in the presence of a catalyst to produce a reaction mixture. The reaction mixture is passed via line 2 to flash separator 102 wherein vapor and liquid phases are separated. The vapor fraction is passed via line 3 to propylene oxide absorber 103 wherein propylene oxide in the vapor is absorbed with a methanol-water mixture fed via line 6 to the absorber. Overhead vapors from absorber 103, except for a small purge, are recycled via line 5 to reactor 101. The liquid stream from flash separator 102 and the liquid stream at the bottom of propylene oxide absorber 103 are passed respectively via lines 4 and 7 to low-pressure depropanizer 104. The depropanized liquid at the bottom of depropanizer 104 is fed via line 9 to crude propylene oxide column 105, wherein crude propylene oxide is distilled as overhead via line 10 for further purification. A residual mixture is obtained as the bottoms stream 11. The residual mixture comprises mostly methanol and water. It may comprise buffer, propylene glycol, propylene glycol ethers, dipropylene glycol ethers, and any other heavy organic components. Small amount of methoxyacetone may also be present. Typically, less than 0.1 wt %, preferably less than 0.01 wt % propylene oxide is present in the residual mixture.

A portion of the residual mixture is recycled to the reaction step. The amount of the residual mixture recycled partly depends on its water content. Generally, 5 to 40 wt %, preferably 10 to 30 wt % of the residual mixture is recycled to the reaction step. Generally the higher the water content, the less amount of residual mixture is recycled.

A portion of the residual mixture is distilled to generate a methanol stream. In FIG. 1, a portion of the residual mixture in line 11 is fed to methanol recovery column 106 via line 15. A methanol stream is recovered as overhead via line 12. The methanol stream typically contains at least 95 wt % methanol. Minor amount of propylene glycol ether, methoxyacetone, and water may be present in the distilled methanol. 1-Methoxy-2-propanol (a propylene glycol methyl ether) and/or methoxyacetone forms azeotropes with water, thus these components may end up in the methanol stream if water is taken overhead. Preferably the methanol stream contains at least 95 wt % methanol, preferably at least 98% methanol.

At least a portion of the methanol stream is recycled to the reaction step. For example, a portion of the methanol stream may be used as an absorbing solvent for the propylene oxide absorber 103.

The bottoms stream from methanol column 106 comprises mostly water, propylene glycol, propylene glycol ethers, and buffer. Typically, it comprises from 60 to 90 wt % water, from 0.5 wt % to 5 wt % buffer, and from 10 to 30 wt % organic components. The bottoms stream may be further processed to recover the buffer. See copending application Ser. No. 12/157,110, filed Jun. 6, 2008.

Comparative Example 1

Propylene Oxide Production

The process is conducted as shown in FIG. 1 except that the gas stream in line 5 is not recycled to the reactor 101.

A catalyst is prepared by following the procedure taught by Example 5 of the copending application Ser. No. 11/891,460, filed on Aug. 10, 2007 now abandoned. 1.6 kg catalyst is charged to a 36-L stainless reactor 101 equipped with feed inlets, reaction mixture outlet, and an agitator.

Fresh propylene, hydrogen, oxygen, nitrogen, and a recycled solvent stream (via line 14 and line 12) are continuously fed to the reactor 101. Total flow rates to the reactor for individual components are propylene (0.44 kg/h), hydrogen (0.04 kg/h), oxygen (0.47 kg/h), nitrogen (0.65 kg/h), methanol (6.38 kg/h), water (1.12 kg/h), and an ammonium phosphate buffer (0.18 kg/h, fed as an aqueous solution). The reaction is operated at 60° C. and 300 psig.

The reaction mixture containing 1.6 wt % propylene, 0.7 wt % propane, 3.5 wt % propylene oxide, 0.04 wt % hydrogen, 0.7 wt % oxygen, 75 wt % methanol, 18 wt % water, 0.06 wt % ammonium phosphate, and nitrogen diluent gas is passed via line 2 to flash separator 102. The liquid stream 4 from flash separator 102 comprises 3.7 wt % propylene oxide, 0.56 wt % propylene, 0.19 wt % propane, 75 wt % methanol, 18 wt % water, and 0.065 wt % ammonium phosphate. The vapor stream comprising 0.43 mole percent (mol %) propylene oxide, 3.0 mol % propane, 5.9 mol % oxygen, 1.5 mol % hydrogen, and 79 mol % nitrogen is passed via line 3 to propylene oxide absorber 103 wherein propylene oxide is absorbed into a methanol-water mixture. The absorber 103 has about 20 theoretical stages. The recycle solvent (obtained as overhead of solvent recovery column 106) is chilled to 15° C. and fed to the top of the absorber 103 at a flow rate of 3 kg/h via line 6. The absorber exit gas (containing primarily propylene, propane, oxygen, hydrogen, and nitrogen) is purged and thermally oxidized via a flameless thermal oxidizer (FTO) manufactured by Thermatrix. Both the absorber bottom liquid effluent (via line 7) and the separator liquid product (via line 4) are fed to depropanizer 104. The depropanizer 104 has 20 theoretical stages. Its overhead temperature is 3° C. and pressure is 10 psig. Its bottom temperature is 82° C. and pressure is 10.2 psig. A C3 stream, comprising mostly propylene and propane exiting the depropanizer 104 via line 8, is thermally oxidized via FTO. The depropanizer liquid stream 9 is fed to crude propylene oxide column 105. The crude propylene oxide column 105 has 44 theoretical stages. Its overhead temperature is 36° C. and pressure is 1.0 psig. Its bottom temperature is 75° C. and pressure is 1.4 psig. Crude propylene oxide is obtained as an overhead distillate via line 10, and further purified to produce commercial grade propylene oxide (not shown). The bottoms stream (residual mixture) comprising 71 wt % methanol, 25 wt % water, propylene oxide derivatives (e.g., propylene glycol, propylene glycol monomethyl ethers, dipropylene glycol, and dipropylene glycol methyl ethers), and ammonium phosphate, exits column 105 via line 11. The residual mixture (8.5 kg/h) is passed via line 15 to solvent recovery column 106. Column 106 has 16 theoretical stages. Its overhead temperature is 72° C. and pressure is about 0 psig. Its bottom temperature is 100.5° C. and pressure is 0.20 psig. A distilled methanol stream containing 13 wt % water and 2 wt % propylene glycol monomethyl ethers is recovered as overhead and is recycled at 7.5 kg/h to the reactor 101 via line 12. The bottoms stream of the solvent-recovery column, comprising 11 wt % propylene glycol monomethyl ethers, 2 wt % propylene glycol, 0.5 wt % heavy glycol and glycol ethers, 0.9 wt % ammonium phosphates, and 85% water, is removed via line 13 for buffer recovery and waste disposal (not shown).

The reaction mixture is analyzed by gas chromatography (GC). The process conditions, analytical results are shown in Table 1. POE and PO productivities are at 0.24 and 0.20 grams PO per gram catalyst per hour (g PO/g cat/h), respectively. PO/POE selectivity is 83% and POE/propylene selectivity is 85%. The catalyst productivity is defined as the grams of propylene oxide formed (including PO subsequently reacted to form propylene oxide derivatives) per gram of catalyst per hour. POE (mole)=moles of propylene oxide+ moles of propylene oxide units in the propylene oxide derivatives. PO/POE=(moles of propylene oxide)/(moles of POE)× 100. Propylene to POE selectivity=(moles of POE)/(moles of propane formed+moles of POE)×100.

Example 2

Propylene Oxide Production

The procedure of Example 1 is continued except that a portion of the residual mixture (3.5 kg/h) from column 105 is recycled directly to reactor 101 via line 14. The rest (5 kg/h) is passed via line 15 to solvent recovery column 106. Column 106 overhead is now controlled at 66° C. instead of 72° C. and pressure is about 0 psig. A distilled methanol stream containing 1-2 wt % water and essentially free of propylene glycol monomethyl ethers is recovered as overhead and is recycled at 4 kg/h to the reactor 101 via line 12. POE and PO productivities are obtained at 0.23 and 0.19 g PO/g cat/h, respectively. PO/POE selectivity is 82% and POE/propylene selectivity is 88%. Water in reactor liquid mixture is maintained at about 18 wt % in both Example 1 and Example 2 but buffer concentrations of ammonium and phosphates are higher in Example 2.

Comparative Example 3

Propylene Oxide Production

The procedure of Example 2 is continued except that a larger portion of the residual mixture (5.5 kg/h) from column 105 is recycled directly to reactor 101 via line 14. The rest (3 kg/h) is passed via line 15 to solvent recovery column 106. As in Example 2, column 106 overhead is controlled at 66° C. instead of 72° C. and pressure is about 0 psig. A distilled methanol stream containing 1-2 wt % water and essentially free of propylene glycol monomethyl ethers is recovered as overhead and is recycled at 2 kg/h to the reactor 101 via line 12. POE and PO productivities obtained are reduced to 0.20 and 0.15 g PO/g cat/h, respectively. PO/POE selectivity is 75% and POE/propylene selectivity is 92%. The result shows higher PO loss due to PO ring-opening reactions. Water in reactor liquid mixture is up to 30 wt % and buffer concentration is built-up further.

Comparative Example 4

Propylene Oxide Production

The procedure of Example 3 is continued except that the undistilled solvent stream is not recycled to the reactor 101 starting at 656 hours-on-stream. POE and PO productivities are restored to 0.24 and 0.20 g PO/g cat/h, respectively. PO/POE selectivity is 83% and POE/propylene selectivity is 88% as water in reactor mixture liquid is returned to about 18 wt %.

From Examples 1 and 2, we conclude that PO and POE productivities are comparable as long as water concentration in the reactor is maintained about the same. Recycling a portion of the undistilled solvent to the reactor does not have any negative effect on productivities or product selectivities. Thus by recycling a portion of the undistilled solvent directly to the epoxidation reactor, both the residual mixture feed to the solvent column 106 and the distilled solvent recovery overhead are reduced, providing capital and energy savings for the production unit. For example, a plant producing 300 metric ton propylene oxide per year using the process of Example 2 needs to use a single atmospheric column of 32 feet in diameter and consumes 800 MMBTU/h energy to operate the column. In contrast, a similar plant with the same capacity using the process of Example 1 needs to use a column of 34 feet in diameter and consumes 1240 MMBTU/h.

The results in Example 3 indicate that higher water concentration in the reactor may lead to lower production rates.

Comparison of Examples 1, 3, and 4 shows that the catalyst activity is restored once a low water concentration condition is returned. Thus the higher water concentration does not result in noticeable permanent catalyst deterioration. It also shows that very little change of catalyst activity and selectivities during the nearly 700-h test.

TABLE 1

Propylene Oxide Production

| | Example | | | |
|---|---|---|---|---|
| | C. 1 | 2 | C. 3 | C. 4 |
| Conditions | | | | |
| Hours on Stream | 393-428 | 453-520 | 556-618 | 656-673 |
| Line 12, Distilled Solvent (kg/h) | 7.5 | 4 | 2 | 7.5 |
| Line 14, Undistilled Solvent (kg/h) | 0 | 3.5 | 5.5 | 0 |
| Percentage of recycle from line 11 to line 14 (%) | 0 | 27 | 42 | 0 |
| Temperature (° C.) | 60 | 60 | 60 | 60 |
| Pressure (psig) | 301 | 300 | 300 | 301 |
| Slurry Concentration (wt %) | 5.6 | 5.6 | 5.6 | 5.5 |
| Fresh $H_2$ Feed (SLPH) | 459 | 442 | 415 | 449 |
| Fresh $O_2$ Feed (SLPH) | 350 | 338 | 317 | 343 |
| Fresh $C_3H_6$ Feed (kg/h) | 0.46 | 0.42 | 0.35 | 0.43 |
| Liquid composition (Line 4), wt % | | | | |
| propylene oxide | 3.7 | 3.4 | 2.8 | 3.5 |
| methanol | 74.6 | 75.4 | 61.6 | 74.2 |
| water | 17.6 | 17.7 | 30.1 | 17.6 |
| 1-methoxy-2-propanol | 2.5 | 1.3 | 2.1 | 3.3 |
| 2-methoxy-1-propanol | 0.5 | 0.9 | 1.6 | 0.5 |
| propylene | 0.56 | 0.55 | 0.31 | 0.54 |
| propane | 0.19 | 0.14 | 0.05 | 0.14 |
| pH | 5.0 | 4.8 | 4.8 | 5.0 |
| calc $PO_4^{-3}$ in Liq. (ppm) | 527 | 1185 | 2271 | 530 |
| calc $NH_4^+$ in Liq. (ppm) | 120 | 270 | 518 | 121 |
| Exit gas composition (Line 3), mol % | | | | |
| hydrogen | 1.5 | 1.8 | 2.3 | 1.8 |
| oxygen | 5.9 | 6.0 | 6.1 | 6.0 |
| nitrogen | 78.6 | 79.6 | 79.7 | 78.9 |
| propylene | 8.1 | 8.1 | 8.1 | 8.1 |
| propane | 3.0 | 2.3 | 1.6 | 2.4 |
| propylene oxide | 0.43 | 0.39 | 0.38 | 0.40 |
| Productivity and selectivity | | | | |
| POE productivity (g PO/g cat/h) | 0.24 | 0.23 | 0.20 | 0.24 |
| PO productivity (g PO/g cat/h) | 0.20 | 0.19 | 0.15 | 0.20 |

TABLE 1-continued

Propylene Oxide Production

| | Example | | | |
|---|---|---|---|---|
| | C. 1 | 2 | C. 3 | C. 4 |
| PO/POE selectivity (%) | 83 | 82 | 75 | 83 |
| POE/propylene selectivity (%) | 85 | 83 | 92 | 88 |

We claim:

1. A process for producing propylene oxide comprising
   (a) reacting propylene, oxygen, and hydrogen in the presence of a catalyst and methanol to produce a reaction mixture comprising propylene oxide;
   (b) separating propylene, oxygen, hydrogen, and propylene oxide from the reaction mixture to generate a residual mixture comprising methanol:
   (c) recycling from 10 to 30 wt % of the residual mixture to step (a);
   (d) separating a portion of the residual mixture to generate a methanol stream; and
   (e) recycling the methanol stream to step (a);
   wherein the reaction mixture comprises methanol and water with a methanol to water weight ratio greater than 7:3.

2. The process of claim 1 wherein the methanol stream comprises at least 95 wt % methanol.

3. The process of claim 1 wherein the methanol stream comprises at least 98 wt % methanol.

4. The process of claim 1 wherein the reaction mixture comprises methanol and water with a methanol to water weight ratio greater than 8:2.

5. The process of claim 1 wherein step (a) is performed in the presence of a buffer.

6. The process of claim 5 wherein the buffer comprises an ammonium ion and a phosphate ion with an ammonium to phosphate molar ratio of from 1:1 to 3:1.

7. The process of claim 1 wherein the catalyst comprises a transition metal zeolite and a noble metal.

8. The process of claim 7 wherein the transition metal zeolite is titanium silicalite-1.

9. The process of claim 7 wherein the noble metal is selected from the group consisting of palladium, platinum, gold, rhenium, silver, and mixtures thereof.

* * * * *